United States Patent [19]

Cohen

[11] Patent Number: 4,539,048

[45] Date of Patent: * Sep. 3, 1985

[54] ALUMINUM ZIRCONIUM METALLO-ORGANIC COMPLEXES USEFUL AS COUPLING AGENTS

[75] Inventor: Lawrence B. Cohen, Sharon, Mass.

[73] Assignee: Jos. Cavedon Company Inc., Woonsocket, R.I.

[*] Notice: The portion of the term of this patent subsequent to Sep. 3, 2002 has been disclaimed.

[21] Appl. No.: 465,207

[22] Filed: Feb. 9, 1983

[51] Int. Cl.$^3$ ................................................. C07F 7/00
[52] U.S. Cl. ........................... 106/287.17; 106/287.19; 524/398; 556/27
[58] Field of Search ........................... 260/429.3, 414; 428/411, 432, 446, 537, 699; 106/287.17, 287.19

[56] References Cited

U.S. PATENT DOCUMENTS

| | | |
|---|---|---|
| 2,832,754 | 4/1958 | Jex et al. . |
| 2,930,809 | 3/1960 | Jex et al. . |
| 2,941,918 | 6/1960 | West . |
| 2,946,701 | 7/1960 | Plueddemann . |
| 3,030,320 | 4/1962 | Haslam . |
| 3,032,570 | 5/1962 | Haslam . |
| 3,044,982 | 7/1962 | Jex et al. . |
| 3,045,036 | 7/1962 | Jex et al. . |
| 3,334,119 | 8/1967 | Cohen . |
| 3,405,153 | 10/1968 | Jones et al. .......................... 260/429.3 |
| 3,419,587 | 12/1968 | Harson .......................... 260/429.3 X |
| 3,553,316 | 1/1971 | Rubino .......................... 260/429.3 X |
| 3,660,134 | 5/1972 | Morris et al. . |
| 3,697,474 | 10/1972 | Morris et al. . |
| 3,697,475 | 10/1972 | Morris et al. . |
| 3,792,068 | 2/1974 | Luedders et al. ................. 260/429.3 |
| 3,981,986 | 9/1976 | Rubino .............................. 260/429.3 |
| 4,017,599 | 4/1977 | Rubino .......................... 260/429.3 X |
| 4,080,353 | 3/1978 | Monte et al. . |
| 4,102,642 | 7/1978 | Banks . |
| 4,141,751 | 2/1979 | Moreland . |
| 4,152,311 | 5/1979 | Monte et al. . |
| 4,223,010 | 9/1980 | Rubino et al. ................ 260/429.3 X |
| 4,360,544 | 11/1982 | Franz .............................. 428/432 X |
| 4,414,275 | 11/1983 | Woods ................................. 428/411 |

OTHER PUBLICATIONS

D. N. Solomon et al., "Chemistry of Pigments and Fillers", 108–78, (John Wiley and Sons, 1983).

*Primary Examiner*—Helen M. S. Sneed
*Attorney, Agent, or Firm*—David G. Conlin; Ernest V. Linek

[57] ABSTRACT

This invention relates to novel compositions of matter which are mixed metal metallo-organic complex agents comprised of a chemically united complex aluminum moiety and tetravalent zirconium moiety. The specific process for preparing such compositions in mixed organic/aqueous media with desirable hydrolytic stability is described.

Further described are compositions of matter wherein the aforementioned metallo-organics are employed as coupling agents to chemically modify the surface of fibrous and particulate inorganic substances and certain organic particulates, thereby resulting in hydrophobic, organophilic fibers and particles having improved rheological properties which facilitate higher filler or fiber loading levels, e.g. in plastics and resins, and serve to enhance the physical properties of composite articles and coatings formed therewith.

23 Claims, 4 Drawing Figures

The organofunctional ligand, —OC(R₂)O— is a moiety which can be derived from one of, or a combination of, the following groups:
(1) An alkyl, alkenyl, alkynyl, aryl or aralkyl carboxylic acid having from 2 to 18 carbon atoms, the preferred range being 2 to 6 carbon atoms;
(2) an aminofunctional carboxylic acid having from 2 to 18 carbon atoms, the preferred range being 2 to 6 carbon atoms;
(3) a dibasic carboxylic acid having from 2 to 18 carbon atoms wherein both carboxy groups are preferably terminal, the preferred range being 2 to 6 carbon atoms; or
(4) acid anhydrides of dibasic acids having from 2 to 18 carbon atoms, the preferred range being 2 to 6 carbon atoms.
(5) A mercapto functional carboxylic acid having from 2 to 18 carbon atoms, the preferred range being 2 to 6 carbon atoms.
(6) An epoxy functional carboxylic acid having from 2 to 18 carbon atoms, preferably from 2 to 6 carbon atoms.

An extensive variety of —OC(R₂)O— anionic ligands is useful in the preparation of the subject compositions. Examples of specific dibasic acids includes anions of: oxalic, malonic, succinic, glutonic, adipic, tartaric, itaconic, maleic, fumaric, phthalic and terephthalic.

Examples of specific aminofunctional carboxylate anions, —OC(R₂)O— include the anions of: glycine, alanine, beta-analine, valine, leucine, isoleucine, phenylalanine, tyrosine, serine, threonine, methionine, cysteine, cystine, proline, hydroxyproline, aspartic, and glutaric acids.

Examples of specific useful monobasic carboxylic acid moieties, —OC(R₂)O— include the anions of the following carboxylic acids: acetic, propionic, butyric, pentanoic, hexanoic, heptanoic, octanoic, dodecanoic, myristic, palmitic, stearic, isostearic, propenoic, 2-methylpropenoic, butenoic, hexenoic, benzoic, cinnammic.

Examples of chelating ligands (—OR₁O—) include: ethylene glycol, propylene glycol, glycerol, etc. Examples of alpha-hydroxy acids R₃′CH(OH)COO— are glycolic, lactic, alpha-hydroxybutyric and tartaric acids, and others are known in the art.

Figure 1:
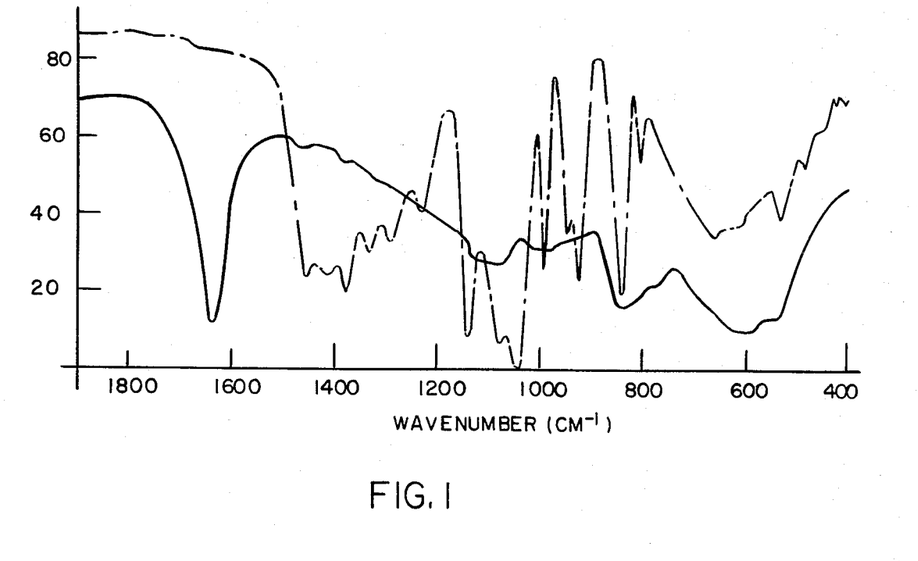
FIG. 1 is a reproduction of an infra red (IR) spectroscopy scan comparing the curves obtained from scanning unreacted propylene glycol (dotted lines) with sec-propanolato aluminum chlorhydrate (solid line).
Figure 2:
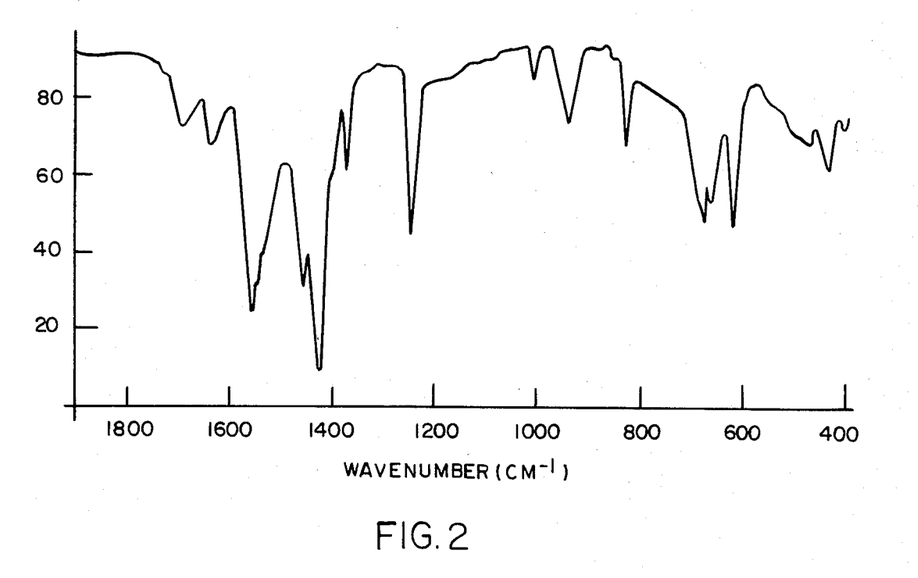
FIG. 2 is the IR scan for the reaction products of methacrylic acid and zirconium oxychloride.
Figure 3:
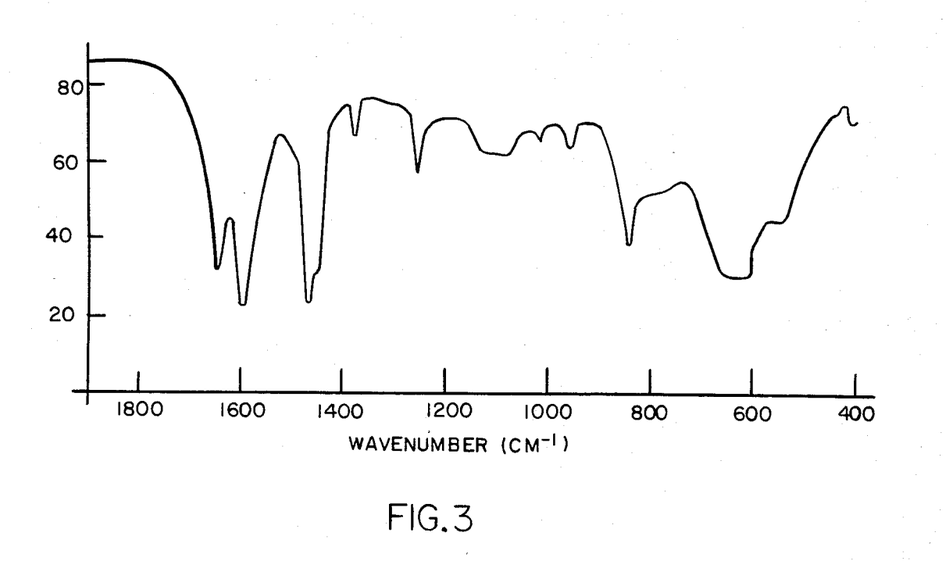
FIG. 3 is the IR scan of the reaction product of methacrylic acid and complexed aluminum chlorhydrate.
Figure 4:
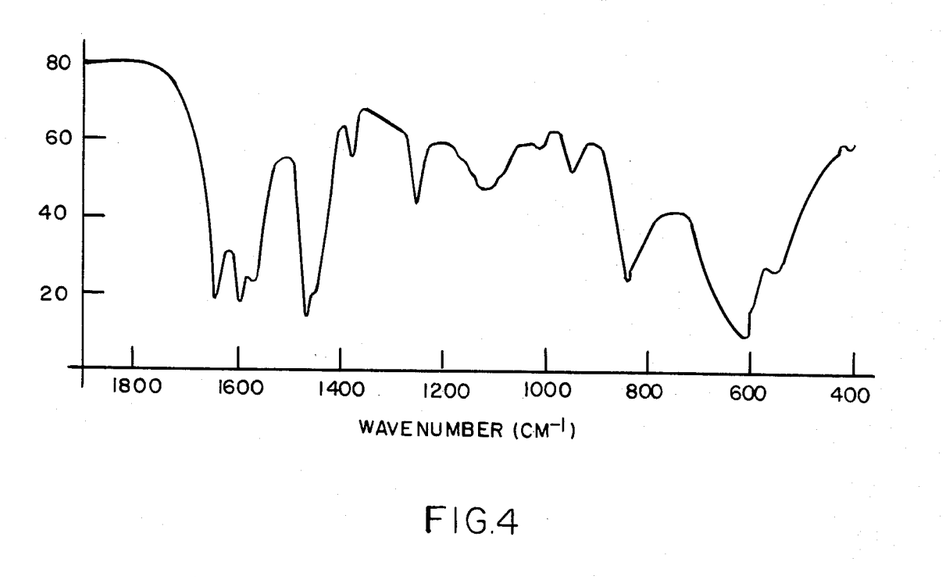
FIG. 4 is the IR scan of the product of Example 2 of the present application.

While not wishing to be bound by theory, characterization of said compositions using infrared spectroscopy (e.g. FIGS. 1 to 4) has indicated that greater than 99% of the organofunctional ligand, —OC(R₂)O— is present in complex form (i.e. has reacted) in the aluminum zirconium metallo-organic and furthermore, that the organofunctional ligands are bound to an aluminum metal center on the one hand and to a zirconium metal center on the other. The IR information also indicates that the chelating agent (—OR₁O—) forms a chelated complex with aluminum.

Thus the reaction product apparently involves the chelated aluminum moiety bridged to the zirconium oxychloride moiety through the organofunctional ligand. This may be empirically represented by formula (IV):

$$[Al_2(OR_1O)_aA_bB_c]_X[OC(R_2)O]_Y[Zr_rA_dB_e]_Z \quad \text{(IV)}$$

wherein A and B are as above-defined, and a,b,c,d and e are as above defined, except that, in order to form the bonds depicted, the substituents attached to the metal groups are appropriately reduced, i.e. 2a+b+c=4 (2a+b+c=5 when the aluminum moiety is a terminal group), and d+e=2 (d+e=3 when zirconium moiety is a terminal group). When the aluminum moiety or the zirconium moiety forms the terminus in the molecular chain, one of the A or B groups may be replaced by a lower alkoxy group having 1 to 6 carbon atoms.

X, Y and Z are at least each 1, and may vary from 1 to 100 or more, depending on the reactivity of the particular materials and the desired form of the product. The molar ratio of aluminum moiety to zirconium moiety (X to Z) may vary from about 1.5 to 10, with the preferred ratio being from about 3 to 6. The ratio of organofunctional ligand to total metal (Y/(2X+Z)) may vary from about 0.05 to 2.0, with the preferred ratio being about 0.1 to 0.5.

The composition cited herein is preferably not prepared in the absence of solvent, in order to avoid encountering undesireable hydrolysis and polymerization reactions which can result in a highly polymeric solid reaction product.

Preparation of the subject composition is preferably attained in a solvent comprised of lower alkyl alcohols having 1 to 6 carbon atoms, lower alkyl ketones having 1 to 6 carbon atoms, or water, preferably, mixtures thereof, wherein the water content is greater than 5%, but less than 20%. Preferably the solvent mixture contains a plurality of lower alkyl alcohols (preferably methanol/isopropanol e.g. 1:1) in an amount of 55-95% by weight, a lower alkyl ketone (preferably acetone) in an amount of 0-20% and water, in the range of about 1-45%. The active matter of compositions so prepared in such solvents is from 10%-65%, preferably from 15%-50%. Pursuant to such preparation the product may be spray dried, freeze dried or otherwise solvent stripped to leave a solid having high activity.

The present invention also provides a process for preparing compositions described above. Hydrolytically stable products having a shelf life in excess of 30 days can be prepared by complexation of a dimeric aluminum chlorohydrate moiety with a bidentate chelating ligand which imparts hydrolytic stability, such as alpha, beta or alpha, gamma glycol, having from 1 to 6 carbon atoms, the preferred ligands having 2 to 3 carbon atoms; or with an alpha-hydroxy carboxylic acid having 2 to 6 carbon atoms. Such complexation should utilize a mole ratio of complexing ligand to Al of 0.05 to 2, the preferred ratio being 0.10 to 1.00. The stabilized aluminum complex can be prepared as either an isolated composition prior to introduction of the zirconium moiety or prepared in situ with zirconium oxychloride, the preferred route being preparation of the stabilized aluminum complex as a separate, isolated composition. Preferably the dimeric aluminum reactant is dissolved in methanol, whereupon propylene glycol is added and the mixture refluxed at 65°-70° C. for one hour to form the stabilized dimeric aluminum complex.

Complexation with —OC(R₂)O—, the organofunctional ligand, can be achieved either upon introduction of the ligand to a solution containing only zirconium oxychloride, or after the introduction and reaction of the zirconium oxychloride with the aforementioned stabilized aluminum chlorohydrate. The reaction should employ a mole ratio of —OC(R₂)O— to total metal of between about 0.05 and 2, the most preferred ratio being from about 0.1 to 0.5. The route elected for snythesis will result in a significant difference in end product composition as characterized by physical and compositional properties, with each type of complex

ALUMINUM ZIRCONIUM METALLO-ORGANIC COMPLEXES USEFUL AS COUPLING AGENTS

BACKGROUND OF THE INVENTION

This invention relates to the manufacture of composite products, such products to be defined as containing chemically dissimilar materials most generally typified by an organic nonpolar substance and an inorganic polar substance. Specifically, the invention describes the preparation and use of novel mixed metal metallo-organic substances which are useful in chemically modifying the particulate or fibrous materials which most often are inorganic for incorporating into the resin matrices with which they will share an interfacial boundary.

It is recognized by those skilled in the art that manufacture of mineral filled or fiber reinforced plastic or rubber articles offers unique problems associated with the poor wetting of the mineral or fiber by the resin. Subsequently, interfacial failure can occur and is augmented in most applications by the presence of moisture which migrates to the interface in the absence of any surface treatment of the mineral filler or fiber and will result in substantial loss in flexural and tensile strength properties. An identical problem is observed in analogous composite systems such as paints and coatings, paper, adhesives, sealants and other compositions containing the organic/inorganic interface.

Historically, fibers, most specifically fiber glass, have been treated with methacrylato chromic chlorides as disclosed in: U.S. Pat. Nos. 2,273,040; 2,524,803; 2,552,910; 2,544,666; 2,544,667; 2,544,668; 2,611,718; and trialkoxy silanes as disclosed in: U.S. Pat. Nos: 2,742,378, 2,776,910, 2,832,754, 2,930,809, 2,946,701, 3,045,036, 3,169,884, 3,211,684, 3,258,477, 3,849,471.

Both of these materials impart additional dry and wet strength properties to glass reinforced fabricated articles. Silanes have also enjoyed usage as a preferred surface treatment for mineral fillers such as silica, alumina trihydrate, mica, wollastonite, and glass beads, when such are to be used in applications wherein physical strength of the composite is an important performance property. More recently, organo titanates, such as described in U.S. Pat. Nos. 4,096,110; 4,098,758; 4,141,751; and 4,152,311 have found some application in mineral filled thermoplastic composites. In other less demanding applications as are found in paper manufacture and some coatings areas it is viable to use surfactants or fatty acid salts to chemically alter the inorganic substrate.

The usefulness of silanes is partially offset by their high cost, a requirement of heat input to react the silanes with fillers, and handling problems related to rapid hydrolysis and polymerization in the presence of moisture, which greatly reduces their effectiveness. Titanates are also hindered by undesireable economics, albeit not as severe as silanes, and also by their limited application in aqueous environments and in products wherein strength properties are significant.

The compositions described herein are unique substances which are highly soluble in water and a variety of polar organics, hydrolytically stable, cost effective viz-a-viz the aforementioned silanes and titanates, and highly reactive, reacting essentially instantaneously with mineral fillers and functional organic particulates at ambient temperature. The said compositions are predicated upon an important symbiotic relationship, which combines the preferred activity of inorganic substrates for the aluminum portion of the molecule and the advantages of using a tetravalent transition metal for purposes of complexation with a reactive organic.

SUMMARY OF THE INVENTION

The subject invention pertains to compositions of matter which are the complex reaction products of (I) chelate-stabilized aluminum compositions (preferably chelate stabilized aluminum chlorohydrates), (II) zirconium oxyhalide (preferably oxychloride) and (III) carboxylic acid(s). The reactants utilized to obtain the compositions of the present invention can generally be represented by the empirical formulas (I), (II), and (III):

$$Al_2(OR_1O)_a A_b B_c \quad \text{(I)}$$

$$ZrA_d B_e \quad \text{(II)}$$

$$\underset{\underset{HO-C=O}{|}}{R_2} \quad \text{(III)}$$

wherein: A and B may be halogen, most preferably chlorine, hydroxy. Preferably A and B are chloro or hydroxy, a is a numerical value ranging from about 0.05 to 2, preferably 0.1 to 1, b is a number ranging from about 0.05 to 5.5, preferably about 1 to 5; and c is a number ranging from 0.05 to 5.5, preferably about 1 to 5, provided that 2a+b+c=6 in the chelate stabilized aluminum reactant. Most preferably A is hydroxy and b ranges from 2 to 5, and B is chlorine and ranges from 1 to 3.8. The variables d and e have a numerical value from 0.05 to 4, provided that d+e=4 in the zirconium oxyhalide metallo-organic complex reactant. Preferably there is at least one hydroxy group and one halogen group in the zirconium reactant. More preferably the empirical ratio of hydroxy to the zirconium in this group is from about 1-2, and the ratio of halogen to zirconium is about 2-3, in that reactant.

In the aluminum containing segment of Formula I, pairs of aluminum atoms are joined by bidentate chelating ligands wherein:

(1) —OR$_1$O— is an alpha, beta or alpha, gamma glycol group in which R$_1$ is an alkyl, alkenyl, or alkynyl group having from 1 to 6 carbon atoms, preferably an alkyl group and preferably having 2 or 3 carbon atoms, such ligands to be used exclusively or in combinations within a given composition, or (2) —OR$_1$O— is an alpha-hydroxy carboxylic acid residue —OCH(R$_3$)—COOH having from 2 to 6 carbon atoms, preferably 2 to 3 carbon atoms (i.e. preferably R$_3$ is H or CH$_3$).

In each instance the organic ligand is bound to two aluminum atoms through two oxygen heteroatoms.

useful in particular types of applications. Preferably the organofunctional ligand is combined with zirconium oxychloride in isopropanol and refluxed at 75°–85° C. for 0.5 hours; whereupon the stabilized dimeric aluminum complex is fed to the mixture over 0.15–0.50 hours. The reaction is completed by a final reflux at 75°–55° C. for 0.50 hours.

It is a further teaching of this invention that the basicity of the dimeric aluminum chlorohydrate moiety critically alters both the reactivity of that moiety with the zirconium moiety and the resultant performance of the aluminum zirconium metallo-organic complex end product. It is understood here that basicity is defined in terms of a divalent Al reactant typified by the general formula:

$$Al_2OH_bCl_c$$

wherein $b+c=6$, basicity is equal to $b/6$. The basicity can be varied from 0 to 5/6 (0.83) by reaction of, for example, the aluminum chlorohydrate with a chloride source exemplified by, but not restricted to, HCl. Preparation of a reduced (less than 5) basicity dimeric aluminum chlorohydrate species with minimal variatons in composition occurs by careful comingling e.g. of hydrochloric acid and aluminum chlorohydrate, so as to maintain a constant temperature of 30° C.–100° C. resulting from the exothermic addition, the preferred temperature being 40° C. to 60° C. It is to be noted that maintenance of the exotherm temperature at less than 30° C. requires an impractically lengthy addition time, whereas an exotherm temperature in excess of 60° C. may result in variant compositions. The reduced basicity product can then be reacted with the aforementioned bidentate ligands, $-OR_1O-$ and $-OCH(R_3)COO-$, resulting in the following compositions:

$$Al_2(R_1O_2)_aOH_bCl_c \text{ or } Al_2(OCH(R_3)COO)_aOH_bCl_c$$

wherein $2a+b+c=6$. In a typical preferred composition, following the reaction of equimolar quantities of hydrochloric acid and dimeric aluminum chlorohydrate, $a=0.25$, $c=3$ and $b=2.50$, and basicity is therefore 0.42.

Compositions prepared in accordance with the teachings of the subject invention are characterized as having a slight yellow color which may range from <50 Pt-Co to Gardner 5 in intensity. Such compositions generally are clear immediately after preparation, but may contain as much as 0.5% insolubles which may be allowed to sediment or removed by conventional filtration techniques.

The active product can be isolated by low vacuum ambient temperature solvent removal, thereby resulting in a highly viscous ($>10^6$ cps) gellatinous mass that, upon complete drying, forms a rigid solid which adheres strongly to glass and resists aqueous dissolution.

Another composition of matter of the invention is the reaction product of the aforementioned aluminum zirconium metallo-organic complexes having the structure as previously described and finely divided inorganic mineral fillers, pigments and fibers. Thus, from 0.02 to 1 phf (parts per hundred filler) of the active product may be chemically reacted with the surface of a particulate inorganic filler material, such materials to include silica, calcium carbonate, alumina trihydrate, aluminum silicates (kaolin and the like), talc, wollastonite, mica or titanium dioxide, resulting in an essentially immediate, largely irreversible alteration in the physical and chemical properties of such particles. On the other hand, dispersion of any of the foregoing particulate minerals in an organic medium in the absence of the composition of the present invention, results in sharp viscosity increase, particle agglomeration, nonuniform distribution, and poor wetting; treatment with the subject aluminum zirconium metallo-organics, either prior to or at the time of introduction of these particulates to the resinous organic medium results in observable improvements in all of these properties. Such improvements afford the use of significantly increased quantities of such mineral particulates while achieving a uniform dispersion of the mineral in the organic matrix. In the specific instance of such particulates being used in a resinous matrix, be it a thermoset, thermoplastic or elastomeric, the resultant fabricated article manufactured with such surface modified particulates will show an improvement in physical strength properties, which is demonstrated, e.g. in the capability of the finished article to transfer an applied stress across the resin particulate interface. While not wishing to be bound by theory, it is believed that the interfacial void which characterizes an untreated filler in contact with a resinous matrix is largely eliminated when the mineral surface has been modified with the subject composition due to:

1. Sizeable changes in the particulate surface energy, thereby leading to enhancement of the wetting of the treated particulate by the resin; and
2. Chemical bonding which occurs between the two dissimilar phases through the intermediacy of the aluminum zirconium metallo-organic, one end of which can attach to the particulate and the other end of which can attach to the resin. Specifically, the chemical nature of the mineral surface, which is often initially highly hydrophilic and organophobic, is modified to produce one which is highly hydrophobic and organophilic.

Although discussion has focused upon the reaction between aluminum/zirconium metallo-organic agents and inorganic mineral fillers, it is a further object of the invention that such complex agents are useful in the modification of particulate organics wherein the organic has pendant reactive groups, i.e. hydroxy or halogen substituents. Thus, by non-limiting example, the subject composition can be employed to alter the surface characteristics of a substance such as tetrabromobisphenol A to render it more readily dispersible in a resinous system, and thereby enhance its efficiency as a flame retardant.

While not wishing to be bound by theory, reaction of the aluminum zirconium metallo-organic agent is believed to occur between the pendant hydroxy or other groups of both aluminum and zirconium metal centers and the filler substrate surface hydroxy groups and/or surface adsorbed molecules of water. The heretofore described modification of the filler surface can be readily effected by any of the following reaction modes:

(1) Dissolution of the aluminum zirconium metallo-organic agent in a suitable solvent, such as water, lower alcohols having fewer than 6 carbon atoms, ketones, carboxylic acids and their esters, tetrahydrofuran, dioxane, dimethylsulfoxide and related organic solvents which are not apolar and subsequent addition of the mineral or organic filler (e.g. 5 to 85 wt percent of total slurry) with concomitant mixing.
(2) Direct addition of the aluminum zirconium metallo-organic agent to a premixed slurry prepared with any of the aforementioned solvents. Such slurries may contain from 5 to 85 wt percent filler.

(3) Direct addition of the aluminum zirconium metalloorganic to the dry filler and high shear agitation such as provided by a Waring Blender to uniformly distribute the treating agent on the filler surface.

Other methods of contacting fillers with the compositions of the present invention will be apparent to those skilled in the art.

Reaction between the filler substrate and the aluminum zirconium metallo-organic agent typically occurs within seconds after contact of the substrate and modifier as effected by low shear mixing (which may include manual agitation) for slurries having an initial viscosity of less than 50,000 cps. An abrupt viscosity reduction to less than 10% of the original viscosity is indicative of the significant change in the surface character of the filler.

The above disclosed inorganic and organic fillers to be used in accordance with the present invention may broadly include particles ranging in size from about 0.05 to 500 microns (equivalent spherical diameter). The preferred range is about 0.5 to 5.0 microns. Where the composition is used with inorganic or organic fibers or filaments, they may also range from about 0.05 to 500 microns (equivalent cylindrical diameter), preferably 0.5 to 50 microns. While some benefit will be obtained from the use of the present aluminum zirconium metallo-organic agents with inorganic or organic fillers of substantially any size, typically the improvement in properties is more substantial and more necessary with the smaller particles.

Another composition of matter which is the subject of this invention is the reaction product of the subject aluminum zirconium metallo-organic agent and glass fibers, either as strands in the forming operation or subsequently as woven fiber glass and woven or non-woven fiber glass mat. The manufacture of fiber glass typically consists of passing the hot glass fibers as they emerge from the forming bushing through an aqueous sizing bath which includes antistatic agents, wetting agents, binders, and, of primary importance in this discussion, coupling (or keying) agents. Such agents in the past have been typified by organosilanes and methacrylato chromic chloride. The subject composition has a capacity to chemically react with both the glass fiber and a resin (most commonly epoxy or unsaturated polyester) and is highly soluble and stable in aqueous media, and therefore can be introduced as a replacement for either the silane and/or the methacrylato chromic chloride. Such substitution will impart to the fiber glass the reactivity necessary for successful use in fiber glass reinforced composites and also the necessary antistatic properties to facilitate handling during the manufacture of the fiber glass and its subsequent use in a variety of fabrication techniques (to include spray gun, hand lay-up, and other commonly encountered methods of fiber glass use).

As detailed in the foregoing discussion, treatment of mineral or organic fillers & pigments, in accordance with the teachings of the subject invention, will permit the usage of elevated levels of such fillers in plastic and elastomeric articles without substantial diminution in physical properties of the finished article, with advantageous reductions in filled resin viscosity, and with attendant cost savings and property benefits. Also similar treatment of mineral fibers (especially glass fibers) and also carbon fibers will enhance performance of such in glass reinforced matrices.

Additionally, the use of such treated fillers and pigments will permit the use of higher filler levels in paints, coatings, binders, sealants and paper manufacture while maintaining product performance. Moreover, essentially the infinite solubility and long term stability of the subject compositions in aqueous media, and the rapid reaction with fillers or pigments at ambient temperature (60° F. to 100° F.) provides the manufacturers of such products with the opportunity to treat the fillers and pigments they use in situ without altering their manufacturing process as well as the option of using a filler which has been pretreated with the aluminum zirconium metallo-organic agent of the present invention. The performance advantages attained in either case are comparable.

EXAMPLE 1

Preparation of Reduced Basicity Sec-Propanolato Aluminum Chlorohydrate

Aluminum chlorohydrate, 1.14 moles Al (123.44 g, 5/6 basic) is dissolved in an equal part of water. Subsequent to complete dissolution, concentrated hydrochloric acid, 112.84 g, is slowly added to the reactor with agitation. The rate of addition is controlled so as to prevent the reaction exotherm from exceeding 50° C.

Thereupon the reaction product is combined with 150 g MeOH. The mixture is brought to reflux, and propylene glycol, 10.88 g (0.143 moles) is fed to the reduced basicity aluminum chlorohydrate, and the system refluxed for 1 hour. The product is indicated by infrared spectroscopy to have a complexed form of propylene glycol.

The spectrum of propylene glycol (neat, broken line in FIG. 1) shows three strong absorbance bands in the 1200–1360 $cm^{-1}$ region at 1230 $cm^{-1}$, 1290 $cm^{-1}$ and 1330 $cm^{-1}$. The latter two bands can be assigned with reasonable certainty to O—H bending vibration modes in the glycol. Upon complexation, the O—H bond is destroyed resulting in the disappearance of such bands as clearly revealed in the spectrum of the propanolato aluminum (solid line). Moreover, the C+O stretching vibrations and related overtone bands found at 840–1230 $cm^{-1}$ have either disappeared or shifted, as seen in the spectrum of the complexed material.

EXAMPLE 2

Preparation of Aluminum Zirconium Metallo Organic Complex

Zirconium oxychloride solution, 0.0339 moles Zr (20.30 g), is combined with 50.00 g of isopropyl alcohol and methacrylic acid, 0.115 moles (9.90 g). The mixture is refluxed for ½ hour to form a partial complex with the zirconium. A 94.9 g portion of the aluminum chloride propylene glycol reaction product of Example I containing 0.197 moles Al, is then fed to a reactor vessel and the reaction completed during a reflux period of ½ hour following the completion of the feed.

Infrared spectroscopy indicates the product thus prepared to be a hybrid complex wherein the methacrylic acid forms a complex bridge between the aluminum and zirconium metal centers.

Methacrylic acid, like most carboxylic acids, is characterized by a strong band at 1700 $cm^{-1}$, representing the —C=O functionality, and by a strong band at 1635 $cm^{-1}$, representing the olefinic function, —C=C—.

Upon complexation, the pi bond becomes delocalized over the 3 atom carboxy system O—C—O, resulting in a weakened C=O bond which is observed as a downfield shift of the carboxy band, and an upfield shift of the olefin band from 1635 cm$^{-1}$ to 1645 cm$^{-1}$. It is noteworthy that upon conversion of methacrylic acid to the corresponding sodium salt that the aforementioned shift of the olefinic absorbance at 1645 cm$^{-1}$ is accompanied by a pronounced reduction in absorption intensity which is not observed when a complex is formed.

Hence, in the subject composition the product of Example 2 is observed to have complex bands at 1570 cm$^{-1}$ and 1595 cm$^{-1}$, (FIG. 4) and also a strong band at 1645 cm$^{-1}$ indicative of the formation of a true complex rather than a salt. The absence of a band at or around 1700 cm$^{-1}$ indicates that virtually all methacrylic acid is present in complex form.

Reaction of methacrylic acid with *only* the zirconium oxychloride moiety (FIG. 2) results in a zirconium methacrylate salt; a carboxy anion band at 1560 cm$^{-1}$ and an accompanying weak olefinic band at 1645 cm$^{-1}$. In like fashion, the reaction of the methacrylic acid with *only* the complex aluminum moiety (FIG. 3) results in a single band at 1595 cm$^{-1}$. It is thus believed that the product composition is a hybrid structure having complex bands at 1570 cm$^{-1}$ and 1595 cm$^{-1}$ wherein the organofunctional group is chemically united to both aluminum and zirconium.

The product thus prepared has the following characteristics: Specific gravity (g/ml)—1.00, Flash Point (COC) °F.°-74° F., Decomposition Point (°C.) >300, Active matter (wt % solids) 17.5, pH (2% solution) 3.50, Aluminum (wt %) 2.95, Zirconium (wt %) 1.70.

were prepared as shown in the accompanying Table I at the indicated concentrations and in the indicated solvents. For example, 400 g of alumina trihydrate (1 micron particle size) is dispersed in 600 g of deionized water using a 4 blade high speed paint agitator. To a 150 g sample of the dispersion containing 60 g of alumina trihydrate having a viscosity of 20,000 cps (Brookfield, Spindle 5, 20 rpm) is added 0.6 g (1.0 phf) of the composition of Example 2 (0.20 phf of active matter). The slurry is agitated manually for 30 seconds at 20° C. whereupon the viscosity is determined to have decreased to 100 cps (Brookfield, Spindle 5, 20 rpm). Seven days later the viscosity of the treated slurry has remained at 100 cps, suggesting substantial irreversibility of the surface modification, (Table I).

Alumina trihydrate was then added in 3 g increments to this sample and viscosity measured, and thereby, 27 g (45% addtional alumina trihydrate) was added before the viscosity increased to the original 20,000 cps.

Alternatively 0.6 g (1.0 phf, 0.20 phf of active matter) of the composition of Example 2, may be dissolved in 90 g of deionized water. Alumina trihydrate, 60 g, is added to the water mix whereupon a slurry having a viscosity of 500 cps results (Brookfield, Spindle 5, 20 rpm.)

As indicated in Table I, surface modification of the indicated mineral fillers with the composition of Example 2 results in pronounced and largely irreversible reductions in filler slurry viscosity in excess of 97 percent. It is further noted that the addition sequence by which a slurry is prepared can markedly effect the observed viscosity. Such is the case with calcium carbonate in alcohol where addition to the slurry is marginally effective (60% viscosity reduction after 7 days) and prior dissolution of surface modifier in solvent results in 99.5% reduction in viscosity.

TABLE I

| FILLER | SOLVENT | SLURRY CONC WT % | Al—Zr SURFACE MODIFIER phf ACTIVE MATTER | ADD'N MODE | VISCOSITY, cps UNTREATED | INITIAL TREATED | 7 DAYS TREATED |
| --- | --- | --- | --- | --- | --- | --- | --- |
| Alumina | Water | 40 | 0.20 | Slurry[1] | 20,000 | 100 | <100 |
| Trihydrate | | | | Solvent[2] | 12,700 | 500 | 500 |
| (1 micron) | Alcohol | 40 | 0.20 | Slurry | 20,000 | <100 | <100 |
| Calcium | Alcohol | 70 | 0.30 | Slurry | 50,000+ | 34,000 | 19,500 |
| Carbonate | | | | Solvent | 50,000+ | 500 | 250 |
| (1 micron) | | | | | | | |
| Silica | Water | | 0.35 | Slurry | 12,000 | 5,500 | 2,750 |
| (1.8 micron) | Alcohol | 70 | 0.03 | Slurry | 13,200 | 300 | 400 |
| | | | | Solvent | 2,100 | 200 | 200 |
| Clay | Alcohol | 70 | 0.30 | Slurry[3] | 20,500 | 750 | 3,500 |
| (4 micron) | | | | Solvent[3] | 21,000 | 250 | 2,250 |
| Titanium | Water | 70 | 0.10 | Slurry | 49,000 | 750 | 500 |
| Dioxide | | | | Solvent | 50,000+ | 750 | 500 |
| (0.5 micron) | Alcohol | | 0.10 | Slurry | 50,000 | 9,250 | 1,000 |

[1]Surface modifier added to filler slurry.
[2]Surface modifier dispersed in solvent, filler added.
[3]Utilized material of Example 7(e), infra. All other results on this table utilized material of Example 2.

EXAMPLE 3

Treatment of Inorganic Mineral Fillers With Aluminum Zirconium Metallo-Organic Surface Modifiers This example teaches the use of compositions of this invention for the surface modification of finely divided inorganic mineral fillers characterized by particle sizes between 0.5 and 5.0 microns. Thus, filler dispersions

EXAMPLE 4–22

Other Aluminum/Zirconium Metallo-Organic Agents

In a manner similar to that detailed for Examples 1 and 2, other aluminum zirconium metallo-organic complex agents were prepared having the substituents and ratios of substituents indicated in Table II below.

TABLE II
MADE UP OF ADDITIONAL COMPLEX GROUPS

| Example | $-OR_1O-$ | $R_2COOH$ | X:Z | Y:(2X + Z) | Basicity of $Al_2A_bB_c$ |
|---|---|---|---|---|---|
| 4 | $-OCH(CH_3)CH_2-O-$ | $CH_2=C(CH_3)COOH$ | 1.5:1 | .25 | 0.5 |
| 5 | " | " | 2:1 | .36 | 0.5 |
| 6 | " | " | 3:1 | .36 | 0.5 |
| 7 (a) | " | " | 4.5:1 | .13 | 0.5 |
| (b) | " | " | 4.5:1 | .53 | 0.5 |
| (c) | " | " | 4.5:1 | .31 | 0.5 |
| (d) | " | " | 4.5:1 | .36 | 0.5 |
| (e) | " | " | 4.5:1 | .24 | 0.5 |
| 8 | " | " | 6:1 | .36 | 0.5 |
| 9 | " | " | 7.5:1 | .36 | 0.5 |
| 10 | " | $CH_2=CH-COOH$ | 3:1 | .36 | 0.42 |
| 11 (a) | " | $NH_2-CH_2CH_2COOH$ | 4.5:1 | .13 | 0.5 |
| (b) | " | $NH_2-CH_2CH_2COOH$ | 4.5:1 | .50 | 0.5 |
| 12 | " | $HOOC-COOH$ | 3:1 | .36 | 0.42 |
| 13 | " | $HOOC\ CH_2COOH$ | 3:1 | .36 | 0.42 |
| 14 | " | $HOOC(CH_2)_2COOH$ | 3:1 | .36 | 0.42 |
| 15 | " | $HOOC(CH_2)_3COOH$ | 3:1 | .36 | 0.42 |
| 16 | " | $HOOC(CH_2)_4COOH$ | 3:1 | .36 | 0.42 |
| 17 | " | $HOOC(CH_2)_4COOH$ | 3:1 | .50 | 0.42 |
| 18 | " | $CH_2=C(CH_3)COOH$ | 4.5:1 | .50 | 0.67 |
| 19 | " | $CH_2=C(CH_3)COOH$ | 3:1 | .50 | 0.67 |
| 20 | " | $CH_2=C(CH_3)COOH$ | 1.5:1 | .50 | 0.67 |
| 21 | $-O-CH_2-COO-$ | $CH_2=C(CH_3)COOH$ | 3:1 | .50 | 0.5 |
| 22 | $-OCH_2-COO-$ | $CH_2=C(CH_3)COOH$ | 4.5:1 | .50 | 0.5 |

All of the compositions provide Aluminum Zirconium Metallo-organic treatment agents which are useful in improving the surface properties of inorganic fillers and like materials. It is also possible to obtain useful compositions using other organic reactants and other Al:Zr ratios and basicities, outside the ranges indicated in Table II, but such products should be checked for stability and effectiveness before use. Preferably, the compositions made in accordance with the present invention have shelf life of at least 30 days.

EXAMPLE 23

Preparation and Use of Inorganic Mineral Filler Pretreated with Aluminum Zirconium Metallo Organic Surface Modifiers A 70 wt % alcoholic dispersion of silica (1.8 micron particle size) is prepared as per the procedure described in Example 3. To the slurry is added 0.15 phf (active matter) of an aluminum zirconium metallo-organic surface modifying agent made with the components and ratios given in connection with Example 7(e) in Table II. The visosity of the untreated and treated slurry is noted (as shown in Table III). The slurry is then placed in a drying oven at 110° C. for 30 minutes to remove solvent whereupon to the dry treated silica is added an amount of alcohol equivalent to that which is removed during the drying process. The silica is redispersed and the viscosity is measured and observed to be equivalent to the analogous slurry prior to drying.

TABLE III
SILICA TREATMENT

| PROCESS DESCRIPTION | SOLVENT | Al—Zr SURFACE MODIFIER phf, ACTIVE MATTER | VISCOSITY, cps |
|---|---|---|---|
| 1. Untreated Silica Slurry | Alcohol | — | 8400 |
| 2. Treated Silica Slurry | Alcohol | 0.15 | 125 |
| 3. Dry Silica | — | — | — |
| 4. Redispersed Treated Silica | Alcohol | 0.15 | 125 |

Thus is shown the permanence of the surface modification and the viability thereby to prepare and supply pretreated fillers for industries heretofore mentioned, i.e., paints and coating, filled plastics, filled elastomers, paper and related industries

EXAMPLE 24

Physical Properties of Fiberglass Reinforced Polyester Laminates

Fiber glass was prepared and treated with an aqueous size bath containing aluminum zirconium metallo-organic coupling agent. Subsequently, fiber glass reinforced polyester laminates were prepared using a U.S. Steel general purpose unsaturated orthophthalic polyester resin, (approx. 70%) and the treated fiber glass (approx. 30%). Two similar fabricated laminates were prepared using commercially available methacrylato chromic chloride and methacrylato silane under identical conditions. The laminates were then evaluated for wet and dry physical properties. The results were as follows:

TABLE IV

| | METHACRYLATO CHROMIC CHLORIDE CONTROL | METHACRYLATO SILANE | Al—Zr COUPLING AGENT 1 | Al—Zr COUPLING AGENT 2 | Al—Zr COUPLING AGENT 3 |
|---|---|---|---|---|---|
| Tensile (Dry) psi | 10,900 | 9,850 | 13,700 | 12,000 | 9,700 |

TABLE IV-continued

|  | METHACRYLATO CHROMIC CHLORIDE CONTROL | METHACRYLATO SILANE | Al—Zr COUPLING AGENT 1 | Al—Zr COUPLING AGENT 2 | Al—Zr COUPLING AGENT 3 |
|---|---|---|---|---|---|
| (Wet)[1] | 9,300 | 8,920 | 9,100 | 10,500 | 10,700 |
| % Retention | 85.5 | 90.6 | 66.2 | 87.8 | 110 |
| Flexural Strength |  |  |  |  |  |
| (Dry) psi | 25,400 | 21,780 | 26,700 | 24,400 | 23,300 |
| (Wet)[1] | 17,700 | 18,660 | 17,800 | 18,100 | 19,000 |
| % Retention | 70.0 | 85.7 | 66.8 | 74.0 | 85.2 |
| Flexural Modulus |  |  |  |  |  |
| (Dry) | $9.14 \times 10^5$ | $7.4 \times 10^5$ | $8.52 \times 10^5$ | $8.14 \times 10^5$ | $9.20 \times 10^5$ |
| (Wet)[1] | $5.86 \times 10^5$ | $6.4 \times 10^5$ | $5.68 \times 10^5$ | $5.94 \times 10^5$ | $6.75 \times 10^5$ |
| % Retention | 64.0 | 86.7 | 66.7 | 73.0 | 73.4 |
| Notched Izod | 11.8 | 14.5 | 13.7 | 10.3 | 10.1 |
| (Dry) |  |  |  |  |  |
| (Wet)[1] | 12.0 | 14.1 | 11.6 | 11.7 | 12.3 |
| % Retention | 102 | 97.3 | 84.7 | 114 | 123 |

[1] $\frac{\text{Dry Strength}}{\text{Wet Strength}} \times 100$, After 24 hours in boiling water The data clearly shows that the aluminum zirconium metallo-organics impart excellent dry strength (tensile, flexural) to such laminates and, more importantly, provide protection from hydrolytic interfacial degradation which is most readily reflected in % retention of both tensile and flexural strength data. The aluminum zirconium metallo-organics are observed to exhibit performance comparable to the methacrylato silane and exceeding the methacrylato chromic chloride.

I claim:

1. A composition of matter comprising the reaction product of a chelated aluminum moiety, an organofunctional ligand and a zirconium oxyhalide, the organofunctional ligand being complexed with and chemically bound to the chelated aluminum moiety and the zirconium moiety, the aluminum moiety having the formula:

$$Al_2(OR_1O)_a A_b B_c$$

wherein A or B is hydroxy or halogen and a, b and c are numerical values such that $2a+b+c=6$, and $(OR_1O)$ is (a) an alpha, beta or alpha, gamma glycol group in which $R_1$ is an alkyl group having 1 to 6 carbon atoms or (b) an alpha-hydroxy carboxylic acid residue having the formula:

$$-O-\underset{\underset{H}{|}}{C}H-\underset{\underset{}{\|}}{C}-O-$$
$$\phantom{-O-}R_3\phantom{H-}O\phantom{-O-}$$

wherein $R_3$ is H or an alkyl group having from 1 to 4 carbon atoms; the organofunctional ligand is (1) an alkyl, alkenyl, alkynyl or aralkyl carboxylic acid having from 2 to 6 carbon atoms, (2) an aminofunctional carboxylic acid having from 2 to 6 carbon atoms, (3) a dibasic carboxylic acid having from 2 to 6 carbon atoms, (4) an acid anhydride of a dibasic acid having from 2 to 6 carbon atoms, (5) a mercapto functional carboxylic acid having from 2 to 6 carbon atoms, or (6) an epoxy functional carboxylic acid having from 2 to 6 carbon atoms; and the zirconium oxyhalide moiety has the formula:

$$ZrA_d B_e$$

wherein A and B are as above-defined and d and e are numerical values such that $d+e=4$; the molar ratio of chelated aluminum moiety to zirconium oxyhalide moiety being from about 1.5 to 10, and the molar ratio of organofunctional ligand to total metal being from about 0.05 to 2.

2. The composition of claim 1, wherein $R_1$ is an alkyl group of 2 or 3 carbon atoms or $$-CH-\underset{\underset{}{\|}}{C}-$$
$$\phantom{-}R_3\phantom{H-}O\phantom{-}$$

and $R_3$ is H or $CH_3$.

3. The composition of claim 1, wherein the reaction product corresponds to the empirical formula:

$$[Al_2(OR_1O)_a A_b B_c]_X [OC(R_2)O]_Y \{ZrA_d B_e\}_Z$$

wherein X, Y and Z are at least 1, $R_2$ is an alkenyl group of 2 to 5 carbon atoms, an aminoalkyl group of 1 to 5 carbon atoms, or an alkyl carboxylic acid group having 1 to 5 carbon atoms, and the ratio of X:Z is from about 2:1 to about 5:1.

4. The composition of claim 3, wherein the ratio of Y:2X+Z is from about 0.1 to about 0.5.

5. The composition of claim 3, wherein X:Z is about 3:1, Y:2X+Z is about 0.5, A is hydroxy, B is chlorine, $R_1$ is n-propyl or isopropyl, $R_2$ is methacrylic acid, a is about 0.25, b is about 2.5, and c is about 3.

6. The composition of claim 3, wherein X:Z is about 4.5:1, Y:2X+Z is about 0.5, A is hydroxy, B is chlorine, $R_1$ has three carbon atoms, $R_2$ COO— is Beta-alanine, a is about 1, b is about 3, and c is about 1.

7. The composition of claim 3 wherein X:Z is about 3:1, Y:2X+Z to about 0.35, A is hydroxy, B is chlorine, $R_1$ has 3 carbon atoms, $R_2$ COO— is adipic acid, a is about 0.25, b is about 2.5 and c is about 3.00.

8. A method of preparing a composition of matter useful as a coupling agent, comprising reacting a chelated aluminum moiety with an organofunctional ligand and a zirconium oxyhalide, the aluminum moiety having the formula:

$$Al_2(OR_1O)_a A_b B_c$$

wherein A or B is hydroxy or halogen and a, b and c are numerical values such that $2a+b+c=6$, and $(OR_1O)$ is (a) an alpha, beta or alpha, gamma glycol group in which $R_1$ is an alkyl, group having 1 to 6 carbon atoms or (b) an alpha-hydroxy carboxylic acid residue having the formula:

wherein R$_3$ is H or an alkyl group having from 1 to 4 carbon atoms;
the organofunctional ligand is (1) an alkyl, alkenyl, alkynyl or aralkyl carboxylic acid having from 2 to 6 carbon atoms, (2) an aminofunctional carboxylic acid having from 2 to 6 carbon atoms, (3) a dibasic carboxylic acid having from 2 to 6 carbon atoms, (4) an acid anhydride of a dibasic acid having from 2 to 6 carbon atoms, (5) a mercapto functional carboxylic acid having from 2 to 6 carbon atoms, or (6) an epoxy functional carboxylic acid having from 2 to 6 carbon atoms; and the zirconium oxyhalide moiety has the formula:

$$ZrA_dB_e$$

wherein A and B are as above-defined and d and e are numerical values such that d+e=4; the molar ratio of chelated aluminum moiety to zirconium oxyhalide moiety being from about 1.5 to 10, and the molar ratio of organofunctional ligand to total metal being from about 0.05 to 2, the reaction being carried out in a solvent comprising about 55–95% lower alkyl alcohols having 1 to 6 carbon atoms, about 0–20% of lower alkyl ketones having 1 to 6 carbon atoms, and about 1–45% water.

9. The method of claim 8, wherein the reaction is carried out in a solvent comprising greater than 5% but less than 20% water.

10. The method of claim 9, wherein R$_1$ is alkyl of 2 or 3 carbon atoms or and R$_3$ is H or CH$_3$.

11. The method of claim 8, wherein the reaction product corresponds to the empirical formula:

wherein X, Y and Z are at least 1, R$_2$ is an alkenyl group of 2 to 5 carbon atoms, an aminoalkyl group of 1 to 5 carbon atoms, or an alkyl carboxylic acid group having 1 to 5 carbon atoms, and the ratio of X:Z is from about 2:1 to about 5:1.

12. The method of claim 9, wherein the ratio of Y:2X+Z is from about 0.1 to about 0.5, R$_1$ is alkyl of 2 or 3 carbon atoms or R$_3$ is H or alkyl of 1 to 4 carbon atoms, and R$_2$ is 2-methyl propenoic acid, propenoic acid, beta-alanine, oxalic acid, malonic acid, succinic acid, glutaric acid or adipic acid.

13. The method of claim 9, further comprising forming the aluminum halohydrate chelate complex by reacting an aluminum halohydrate with a bidentate chelating agent having the formula HOR$_1$OH, wherein R$_1$ is an alkyl, alkenyl or alkynyl group having from 1 to 6 carbon atoms, or where R$_3$ is H or an alkyl group having from 1 to 4 carbon atoms.

14. The method of claim 13, where the aluminum halohydrate is aluminum chlorohydrate, having a basicity of from 0 to 0.83.

15. The method of claim 13, wherein the reaction between the aluminum halohydrate and the bidentate chelating agent is conducted in a solvent selected from water, alkyl alcohols and ketones having from 1 to 6 carbon atoms, and mixtures thereof.

16. The method of claim 13, where the chelated aluminum moiety, organofunctional ligand and zirconium oxyhalide are reacted in a solvent which is a mixture of water, an alkyl alcohol having from 1 to 3 carbon atoms, and an alkyl ketone having from 1 to 3 carbon atoms, the final concentration of coupling agent in the solvent being from about 15 to 50 percent.

17. A composition comprising the product of admixture of:
(I) the reaction product of a chelated aluminum moiety, an organofunctional ligand and a zirconium oxyhalide, the organofunctional ligand being complexed with and chemically bound to the chelated aluminum moiety and the zirconium moiety, the aluminum moiety having the formula:

wherein A or B is hydroxy or halogen and a, b and c are numerical values such that 2a+b+c=6, and (OR$_1$O) is (a) an alpha, beta or alpha, gamma glycol group in which R$_1$ is an alkyl group having 1 to 6 carbon atoms or (b) an alpha-hydroxy carboxylic acid residue having the formula:

wherein R$_3$ is H or an alkyl group having from 1 to 4 carbon atoms; the organofunctional ligand is (1) an alkyl, alkenyl, alkynyl or aralkyl carboxylic acid having from 2 to 6 carbon atoms, (2) an aminofunctional carboxylic acid having from 2 to 6 carbon atoms, (3) a dibasic carboxylic acid having from 2 to 6 carbon atoms, (4) an acid anhydride of a dibasic acid having from 2 to 6 carbon atoms, (5) a mercapto functional carboxylic acid having from 2 to 6 carbon atoms, or (6) an epoxy functional carboxylic acid having from 2 to 6 carbon atoms; and the zirconium oxyhalide moiety has the formula:

wherein A and B are as above-defined and d and e are numerical values such that d+e=4; the molar ratio of chelated aluminum moiety to zirconium oxyhalide moiety being from about 1.5 to 10, and the molar ratio of organofunctional ligand to total metal being from about 0.05 to 2, and (II) a filler selected from the group of glass, silica, calcium carbonate, alumina trihydrate, aluminum silicate, talc, wollastonite, mica, titanium dioxide, and an organic particulate having reactive groups.

18. The composition of claim 17, wherein the reaction product corresponds to the empirical formula:

$$[Al_2(OR_1O)_a A_b B_c]_X [OC(R_2)O]_Y [ZrA_d B_e]_Z$$

wherein X, Y and Z are at least 1, $R_2$ is an alkyl, aralkyl, alkenyl alkynyl, aminoalkyl, carboxyalkyl, mercaptoalkyl, or epoxyalkyl group, having from 1 to 6 carbon atoms, and the ratio of X:Z is from about 1.5 to about 5.

19. The composition of claim 18, wherein the inorganic filler comprises glass fibers.

20. A composite product, comprising the composition of claim 18 and a resin selected from the group of thermoset, thermoplastic and elastomeric resins.

21. The composition of claim 18, wherein X:Z is about 3:1, Y:2X+Z is about 0.5, A is hydroxy, B is chlorine, $R_1$ is n-propyl or isopropyl, $R_2$ is methacrylic acid, a is about 0.25, b is about 2.5, and c is about 3.

22. The composition of claim 18, wherein X:Z is about 4.5:1, Y:2X+Z is about 0.5, A is hydroxy, B is chlorine, $R_1$ has three carbon atoms, $R_2$COO— is Beta-alanine, a is about 1, b is about 3, and c is about 1.

23. The composition of claim 18, wherein X:Z is about 3:1, Y:2X+Z is about 0.35, A is hydroxy, B is chlorine, $R_1$ has 3 carbon atoms, $R_2$COO— is adipic acid, a is about 0.25, b is about 2.5, and c is about 3.00.

* * * * *